United States Patent
Nakatsuka et al.

(10) Patent No.: US 7,655,722 B2
(45) Date of Patent: Feb. 2, 2010

(54) ADHESIVE COMPOSITION

(75) Inventors: Kazumitsu Nakatsuka, Hoechst Industrial Park (DE); Naoki Nishigaki, Kurashiki (JP); Mitsunobu Kawashima, Kurashiki (JP)

(73) Assignee: Kuraray Medical Inc., Kurashiki-shi (JP)

(*) Notice: Subject to any disclaimer, the term of this patent is extended or adjusted under 35 U.S.C. 154(b) by 110 days.

(21) Appl. No.: 11/911,849

(22) PCT Filed: Apr. 13, 2006

(86) PCT No.: PCT/JP2006/307807
§ 371 (c)(1),
(2), (4) Date: Oct. 18, 2007

(87) PCT Pub. No.: WO2006/115065
PCT Pub. Date: Nov. 2, 2006

(65) Prior Publication Data
US 2009/0023856 A1 Jan. 22, 2009

(30) Foreign Application Priority Data
Apr. 19, 2005 (JP) .................. 2005-121481

(51) Int. Cl.
*C08L 31/00* (2006.01)
(52) U.S. Cl. .............. 524/546; 524/356; 524/379; 524/544; 524/556; 524/599; 526/208; 526/210; 526/213; 526/245; 526/292.3; 526/319; 562/24; 562/25; 568/16; 570/189; 570/261
(58) Field of Classification Search ............. 524/546
See application file for complete search history.

(56) References Cited

U.S. PATENT DOCUMENTS

2007/0100020 A1    5/2007    Nakatsuka et al.

FOREIGN PATENT DOCUMENTS

| JP | 47-50093 | 12/1972 |
|---|---|---|
| JP | 58-021687 | 2/1983 |
| JP | 58-021607 | 8/1983 |
| JP | 61-176506 | 8/1986 |
| JP | 63-051308 | 3/1988 |
| JP | 2002-038105 | 2/2002 |
| JP | 2002-214741 | 7/2002 |
| JP | 2003-021881 | 1/2003 |

OTHER PUBLICATIONS

"Natural number", Merriam-Webster, http://www.merriam-webste.com/dictionary/natural%20number, retrieved from internet Mar. 11, 2009, 2 pages.*

* cited by examiner

*Primary Examiner*—Marc S Zimmer
*Assistant Examiner*—Nicole M Buie
(74) *Attorney, Agent, or Firm*—Oblon, Spivak, McClelland, Maier & Neustadt, L.L.P.

(57) ABSTRACT

The present invention relates to adhesive compositions having: a phosphate group-containing monomer (a) having a fluorocarbon group represented by Chemical Formula 1; and a solvent (b), (1)

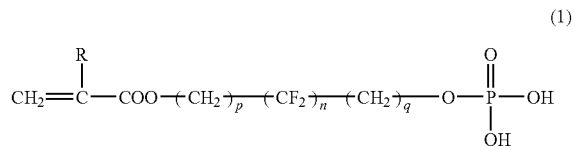

where R is a hydrogen atom or a methyl group, n, p and q are natural numbers $2 \leq n \leq 10$, $p+q \leq n$ and $p+q+n \leq 13$.

18 Claims, No Drawings

ADHESIVE COMPOSITION

CROSS REFERENCE TO RELATED APPLICATION

This application is a 371 of PCT/JP06/307807, filed on Apr. 13, 2006, and claims priority to Japanese Patent Application No. 2005-121481, filed on Apr. 19, 2005.

TECHNICAL FIELD

The present invention relates to an adhesive composition suitably used in the fields of medical care, electronic industry, precision machinery industry, jewel industry and so on.

BACKGROUND ART

In the odontotherapy, a metal cast of an alloy or the like, porcelain, a composite resin or a combination of any of them is used as a restorative material for a defective tooth. In particular, a metal cast is widely used as a restorative material in the odontotherapy because it has high mechanical strength and is easily fabricated. A metal restorative material may, however, degrade the esthetic property of a mouth cavity. Therefore, examinations are recently being earnestly made on improvement of mechanical strength of a composite resin and a ceramic material, which are poor in the mechanical strength but have a high esthetic property. As a result of the examinations, a composite resin-based material including a large amount of inorganic filler (designated as "hybrid ceramics" in general) and metal oxide-based high strength ceramics including a metal oxide of zirconia ($ZrO_2$) or the like as a principal component have been proposed as novel materials for a crown. As a dental adhesive for adhering such a novel crown material onto dentine, a dental resin cement is currently principally used.

As a dental adhesive for adhering the novel material onto dentine, in addition to the dental resin cement, for example, a dental adhesive including a phosphate group-containing monomer disclosed in Patent Document 1 specified below, a dental adhesive composition including a phosphate group-containing monomer and a silane coupling agent disclosed in Patent Document 2 specified below or the like can be used.

Patent Document 1: Japanese Laid-Open Patent Publication No. Sho 58-21607 (Claim 1 on p. 1)

Patent Document 2: Japanese Laid-Open Patent Publication No. Sho 63-51308 (Claim 1 on p. 1)

DISCLOSURE OF INVENTION

Problems to be Solved by Invention

The dental resin cement cannot exhibit sufficient bond strength and adhesive durability as a dental adhesive for adhering the aforementioned novel type of crown materials onto dentine.

Each of the dental adhesive disclosed in Patent Document 1 and the dental adhesive composition disclosed in Patent Document 2 exhibits high bond strength to some extent on the novel type materials. However, when cured substances of them are subjected to thermal cycle load in which they are immersed alternately in cool water and warm water, the bond strength is lowered in a small number of cycles. In other words, the adhesive durability is not sufficient. Therefore, there is a strong demand for improvement in the adhesive durability (persistence of bond strength) of the dental adhesive materials.

The present invention was devised for meeting the demand, and an object of the invention is providing an adhesive composition suitably used in the fields of medical care, electronic industry, precision machinery industry, jewel industry and so on, and in particular, an adhesive composition that exhibits high adhesive durability on a dental restorative material such as ceramics, a composite resin cured substance, porcelain or a metal, and in particular, on a recently attended novel dental material such as the hybrid ceramics or the metal oxide-based high strength ceramics.

Means for Solving Problems

In order to achieve the object, the adhesive composition according to Claim 1 includes a phosphate group-containing monomer (a) including a fluorocarbon group represented by the following Chemical Formula 1; and a solvent (b), Chemical Formula 1:

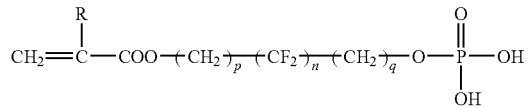

[wherein R is a hydrogen atom or a methyl group, n, p and q are natural numbers, $2 \leq n \leq 10$, $p+q \leq n$ and $p+q+n \leq 13$.]

The adhesive composition according to Claim 2 further includes a coupling agent (c) in the adhesive composition of Claim 1.

The adhesive composition according to Claim 3 further includes a polymerization initiator (d) and/or a polymerization promoter (e) in the adhesive composition of Claim 1 or 2.

The adhesive composition according to Claim 4 further includes a filler (f) in the adhesive composition of any of Claims 1 through 3.

Herein, the adhesive compositions according to Claims 1 through 4 are generically designated as the adhesive composition of this invention.

EFFECT OF INVENTION

The present invention provides an adhesive composition that is suitably used in the fields of medical care, electronic industry, precision machinery industry, jewel industry and so on, exhibits high bond strength and high adhesive durability and is minimally varied in the bond strength. Since the adhesive composition of this invention exhibits high adhesive durability and high coloring resistance on a dental restorative material such as ceramics, a composite resin cured substance, porcelain or a metal, and in particular, on a novel dental restorative material such as the hybrid ceramics or the metal oxide-based high strength ceramics, it is suitably used in the dental field.

BEST MODE FOR CARRYING OUT INVENTION

The adhesive composition of this invention includes a phosphate group-containing monomer (a) including a fluorocarbon group represented by the aforementioned Chemical Formula 1 and a solvent (b).

In the phosphate group-containing monomer (a) including a fluorocarbon group of this invention, n, p and q of Chemical Formula 1 are specified to satisfy relationships of $2 \leq n \leq 10$ and $p+q \leq n$ because these two relational formulas should be satisfied for exhibiting high bond strength and high adhesive durability. Furthermore, in the phosphate group-containing monomer (a), n, p and q of Chemical Formula 1 are specified to satisfy a relationship of p+q+n≦13 because when p+q+n>13, the solubility in the solvent is so low that the composition is inhomogeneous and is varied in the bond strength.

One of phosphate group-containing monomers (a) including a fluorocarbon group may be singly used or a plurality of them may be used together. No matter whether the content of the phosphate group-containing monomer (a) including a fluorocarbon group is too large or too small, the bond strength may be lowered. The content of the phosphate group-containing monomer (a) is generally 0.001 through 99 wt %, preferably 0.01 through 90 wt % and more preferably 0.1 through 85 wt % based on the total weight of the adhesive composition.

The solvent (b) of this invention is not particularly specified as far as the phosphate group-containing monomer (a) including a fluorocarbon group can be dissolved or uniformly dispersed therein. Suitable examples of the solvent (b) are a volatile solvent (b-1) and a monomer (b-2).

At this point, the volatile solvent (b-1) is a solvent with a boiling point at normal pressure of 150° C. or less, and a volatile solvent with a boiling point at normal pressure of 110° C. or less is particularly preferred. Examples of the volatile solvent with a boiling point at normal pressure of 110° C. or less are water, alcohols such as ethanol, methanol, 1-propanol and isopropyl alcohol, ketones such as acetone and methyl ethyl ketone, esters such as ethyl acetate, methyl acetate, ethyl propionate and methyl methacrylate, ethers such as 1,2-dimethoxyethane, 1,2-diethoxyethane and tetrahydrofuran, hydrocarbons such as heptane, hexane and toluene, and halogenated hydrocarbons such as chloroform and dichloromethane. In particular, ethanol, isopropyl alcohol, acetone, methyl methacrylate and water are preferred. In general, the volatile solvent (b-1) is preferably perspired as much as possible with a dental air syringe or the like after application of the adhesive composition.

Specific examples of the monomer (b-2) are as follows, in which a monomer having one olefin double bond is designated as a monofunctional monomer, and monomers are respectively designated as a bifunctional monomer, a trifunctional monomer and so on in accordance with the number of olefin double bonds included therein. It is noted that methacrylate and acrylate are comprehensively mentioned as (meth)acrylate and methacryloyl and acryloyl are comprehensively mentioned as (meth)acryloyl in the following examples:

Monofunctional Monomers:
2-hydroxyethyl(meth)acrylate, 2-hydroxypropyl(meth)acrylate, 3-hydroxypropyl(meth)acrylate, 2-hydroxy-1-(hydroxymethyl)ethyl(meth)acrylate, 2,3-dihydroxypropyl(meth)acrylate, methyl(meth)acrylate, ethyl(meth)acrylate, propyl(meth)acrylate, isopropyl(meth)acrylate, butyl(meth)acrylate, isobutyl(meth)acrylate, benzyl(meth)acrylate, lauryl(meth)acrylate, 2,3-dibromopropyl(meth)acrylate, methacrylamide, acrylamide, 2-hydroxyethylmethacrylamide, 2-hydroxyethylacrylamide Bifunctional Monomers:
ethylene glycol di(meth)acrylate, triethylene glycol di(meth)acrylate, dipentaerythritol di(meth)acrylate, polyethylene glycol di(meth)acrylate (having 9, 14 or 23 oxyethylene groups), propylene glycol di(meth)acrylate, neopentyl glycol di(meth)acrylate, 1,6-hexanediol di(meth)acrylate, 1,10-decanediol di(meth)acrylate, bisphenol A diglycidyl methacrylate (known by the name of "Bis-GMA"), 2,2-bis[4-(meth)acryloyloxyethoxyphenyl]propane, 2,2-bis[4-(meth)acryloyloxypolyethoxyphenyl]propane, 2,2-bis[4-[3-(meth)acryloyloxy-2-hydroxypropoxy]phenyl]propane, 1,2-bis[3-(meth)acryloyloxy-2-hydropropoxy]ethane, pentaerythritol di(meth)acrylate, 1,2-bis(3-methacryloyloxy-2-hydroxypropoxy)ethane, [2,2,4-trimethylhexamethylenebis(2-carbamoyloxyethyl)]dimethacrylate (known by the name of "UDMA"), 1,3-di(meth)acryloyloxy-2-hydroxypropane Tri- or Multi Functional Monomers:
trimethylolpropane tri(meth)acrylate, trimethylolethane tri(meth)acrylate, tetramethylolmethane tri(meth)acrylate, pentaerythritol tetra(meth)acrylate, N,N'-(2,2,4-trimethylhexamethylene)bis[2-(aminocarbonyloxy)propane-1,3-diol] tetramethacrylate, 1,7-diacryloyloxy-2,2,6,6-tetraacryloyloxymethyl-4-oxyheptane One of these solvents (b) may be singly used or a plurality of them may be used together. No matter whether the content of the solvent (b) is too large or too small, the bond strength onto ceramics or a metal may be lowered. The content of the solvent (b) is generally 1 through 99.999 wt %, preferably 10 through 99.99 wt % and more preferably 15 through 99.9 wt % based on the total weight of the adhesive composition.

The adhesive composition of the invention may include a coupling agent (c) for the purpose of improving the bond strength onto an adherend of ceramics, porcelain or a metal. As the coupling agent (c), any of known coupling agents can be used. Specific examples are silane coupling agents such as methyltrimethoxysilane, methyltriethoxysilane, methyltrichlorosilane, dimethyldichlorosilane, trimethylchlorosilane, vinyltrimethoxysilane, vinyltriethoxysilane, vinyltrichlorosilane, vinyltriacetoxysilane, vinyltri(β-methoxyethoxy)silane, 3-(meth)acryloyloxypropyltrimethoxysilane, 3-(meth)acryloyloxypropyltriethoxysilane, 6-(meth)acryloyloxyhexyltrimethoxysilane, 6-(meth)acryloyloxyhexyltriethoxysilane, 10-(meth)acryloyloxydecyltrimethoxysilane, 10-(meth)acryloyloxydecyltriethoxysilane, 11-(meth)acryloyloxyundecyltrimethoxysilane, 11-(meth)acryloyloxyundecyltriethoxysilane, 3-(meth)acryloyloxypropylpentamethyldisiloxane, 3-chloropropyltrimethoxysilane, mercaptopropyltrimethoxysilane and hexamethyldisilazane; titanate-based coupling agents such as isopropyl triisostearoyl titanate, isopropyl trioctanoyl titanate, isopropyl isostearoyl diacryl titanate, isopropyl tridecyl benzene sulfonyl titanate, isopropyl dimethacryloyl isostearoyl titanate and isopropyl tricumyl phenyl titanate; and an aluminum-based coupling agent such as acetoalkoxy aluminum diisopropylate.

Among these exemplified coupling agents, a coupling agent including a polymeric group is preferred from the viewpoint of the adhesive property and the handling property. Examples of the coupling agent including a polymeric group are silane coupling agents including a (meth)acryloyl group such as 3-(meth)acryloyloxypropyltrimethoxysilane, 3-(meth)acryloyloxypropyltriethoxysilane, 6-(meth)acryloyloxyhexyltrimethoxysilane, 6-(meth)acryloyloxyhexyltriethoxysilane, 10-(meth)acryloyloxydecyltrimethoxysilane, 10-(meth)acryloyloxydecyltriethoxysilane, 11-(meth)acryloyloxyundecyltrimethoxysilane and 11-(meth)acryloyloxyundecyltriethoxysilane.

One of the coupling agents (c) may be singly used or a plurality of them may be used together. The coupling agent (c) may be directly included in the adhesive composition of this invention or may be included after transforming it into, for example, a silanol compound or the like by hydrolyzing it with an acid or alkali. Alternatively, a silane coupling agent in which silyl groups are hydrolyzed with time so as to change a part or the whole of the silyl groups into silanol groups may be included. When the content of the coupling agent (c) is excessive, the bond strength onto an adherend of ceramics, porcelain or a metal may be lowered. The content of the coupling agent (c) is preferably 0.01 through 90 wt %, more preferably 0.1 through 50 wt % and most preferably 1 through 30 wt % based on the total weight of the adhesive composition.

The adhesive composition of this invention may include a polymerization initiator (d) for the purpose of improving the polymeric property. Examples of the polymerization initiator (d) are α-diketones, ketals, thioxanthones, acylphosphine oxides, coumarins, a halomethyl-s-triazine derivative and an organic peroxide.

Specific examples of the α-diketones are camphorquinone, benzyl and 2,3-pentanedione. Specific examples of the ketals are benzyl dimethyl ketal and benzyl diethyl ketal. Specific examples of the thioxanthones are 2-chlorothioxanthone and 2,4-diethylthioxanthone. Specific examples of the acylphosphine oxides are 2,4,6-trimethylbenzoyldiphenylphosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, bis(2,4,6-trimethylbenzoyl)phenylphosphine oxide, bis(2,6-dimethylbenzoyl) phenylphosphine oxide, bis(2,6-dimethoxybenzoyl) phenylphosphine oxide, tris(2,4,6-trimethylbenzoyl) phosphine oxide, benzoylbis(2,6-dimethylphenyl) phosphonate and 2,4,6-trimethylbenzoylethoxyphenylphosphine oxide.

Examples of the coumarins are 3,3'-carbonylbis(7-diethylamino)coumarin, 3-(4-methoxybenzoyl)coumarin and 3-tyenoyl coumarin. Examples of the halomethyl-s-triazine derivative are 2,4,6-tris(trichloromethyl)-s-triazine, 2,4,6-tris(tribromomethyl)-s-triazine and 2-methyl-4,6-bis(trichloromethyl)-s-triazine.

Examples of the organic peroxide are diacyl peroxides, peroxy esters, dialkyl peroxides, peroxy ketals, ketone peroxides and hydroperoxides. Specific examples of the diacyl peroxides are benzoyl peroxide, 2,4-dichlorobenzoyl peroxide and m-toluoyl peroxide. Specific examples of the peroxy esters are t-butyl peroxybenzoate, bis-t-butyl peroxyisophthalate, 2,5-dimethyl-2,5-bis(benzoylperoxy)hexane, t-butyl peroxy-2-ethyl hexanoate and t-butyl peroxyisopropyl carbonate. Specific examples of the dialkyl peroxides are dicumyl peroxide, di-t-butyl peroxide and lauroyl peroxide. Specific examples of the peroxy ketals are 1,1-bis(t-butylperoxy)-3,3,5-trimethylcyclohexane, 1,1-bis(t-butylperoxy) cyclohexane and 1,1-bis(t-hexylperoxy)cyclohexane. Specific examples of the ketone peroxides are methyl ethyl ketone peroxide, cyclohexanone peroxide and methyl acetoacetate peroxide. Specific examples of the hydroperoxides are t-butyl hydroperoxide, cumene hydroperoxide and p-diisopropyl benzene hydroperoxide.

In the case where polymerization is caused through UV irradiation, benzoinalkyl ether or benzyldimethyl ketal is suitably used as the polymerization initiator. One of the polymerization initiators (d) may be singly used or a plurality of them may be used together. The content of the polymerization initiator (d) is preferably 0.01 through 10 wt % and more preferably 0.1 through 5 wt % based on the total weight of the adhesive composition.

The adhesive composition of this invention may include a polymerization promoter (e) for the purpose of improving the polymeric property. Examples of the polymerization promoter (e) are tertiary amines, aldehydes, a compound having a thiol group, sulfinic acid and salts thereof.

Specific examples of the tertiary amines are N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-dibutylaniline, n-butoxyethyl 4-dimethylaminobenzoate, (2-methacryloyloxy)ethyl 4-dimethylaminobenzoate, ethyl 4-dimethylaminobenzoate, butyl 4-dimethylaminobenzoate, N-methyl diethanol amine, 4-dimethylaminobenzophenone, trimethylamine, triethylamine, N-methyldiethanolamine, N-ethyldiethanolamine, N-n-butyldiethanolamine, N-lauryldiethanolamine, triethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate and triethanolamine trimethacrylate.

Specific examples of the aldehydes are dimethylaminobenzaldehyde and terephthalaldehyde.

Specific examples of the compound having a thiol group are 2-mercaptobenzooxazole, decanethiol, 3-mercaptopropyltrimethoxysilane and thiobenzoic acid.

Specific examples of the sulfinic acid and salts thereof are benzenesulfinic acid, sodium benzenesulfinate, potassium benzenesulfinate, calcium benzenesulfinate, lithium benzenesulfinate, toluenesulfinic acid, sodium toluenesulfinate, potassium toluenesulfinate, calcium toluenesulfinate, lithium toluenesulfinate, 2,4,6-trimethylbenzenesulfinic acid, sodium 2,4,6-trimethylbenzenesulfinate, potassium 2,4,6-trimethylbenzenesulfinate, calcium 2,4,6-trimethylbenzenesulfinate, lithium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate and calcium 2,4,6-triisopropylbenzenesulfinate.

One of the polymerization promoters (e) may be singly used or a plurality of them may be used together. The content of the polymerization promoter (e) is preferably 0.01 through 10 wt %, more preferably 0.05 through 7 wt % and most preferably 0.1 through 5 wt % based on the total weight of the adhesive composition.

The adhesive composition of this invention may include a filler (f) for improving the mechanical strength, the shielding property, the application property and the like. Examples of the filler (f) are an inorganic filler, an organic filler and an organic/inorganic complex filler. Examples of the inorganic filler are silica; a mineral including silica as a matrix such as kaoline, clay, isinglass or mica; ceramics including silica as a matrix and further including $Al_2O_3$, $B_2O_3$, $TiO_2$, $ZrO_2$, $BaO$, $La_2O_3$, $SrO_2$, $CaO$, $P_2O_5$ or the like; and glass (such as lanthanum glass, barium glass, strontium glass, soda glass, lithium borosilicate glass, zinc glass, fluoroalumino borosilicate glass, borosilicate glass or bioglass). Furthermore, crystalline quartz, hydroxy-apatite, alumina, titanium oxide, yttrium oxide, zirconia, calcium phosphate, barium sulfate or aluminum hydroxide is also preferably used as the inorganic filler. Examples of the organic filler are organic resins such as polymethyl methacrylate, a polymer of polyfunctional methacrylate, polyamide, polystyrene, polyvinyl chloride, chloroprene rubber, nitrile rubber and styrene-butadiene rubber. Examples of the organic/inorganic complex filler are a filler obtained by dispersing any of inorganic fillers in any of the organic resins and any of the inorganic fillers coated with any of the organic resins.

The filler (f) may be included after being treated with a known surface-treatment agent such as a silane coupling agent for the purpose of improving the operability, the application property, the flowability of the adhesive composition and the mechanical strength of a cured substance. Examples of the surface-treatment agent are vinyltrimethoxysilane, vinyltriethoxysilane, vinyltrichlorosilane, vinyltri(β-methoxyethoxy)silane, γ-methacryloyloxypropyltrimethoxysilane, γ-glycidoxypropyltrimethoxysilane, γ-mercaptopropyltrimethoxysilane and γ-aminopropyltriethoxysilane. One of the fillers (f) may be singly used or a plurality of them may be used together. The content of the filler (f) depends upon the application of the adhesive composition, namely, the use of the adhesive composition. For example, in the case where the adhesive composition of the invention is used as an adhesive for filling, the content of the filler (f) is preferably 40 wt % or less, more preferably 30 wt % or less and most preferably 20 wt % or less based on the total weight of the composition. Alternatively, in the case where the adhesive composition of the invention is used as a coherent agent, namely, as a cement, the content of the filler (f) is preferably 30 through 90 wt %, more preferably 40 through 85 wt % and most preferably 50 through 80 wt %. When the filler is used in the coherent agent, it preferably has an average particle diameter of 30 μm or less so as not to make the coating thickness large, and a filler with X-ray impermeability such as lanthanum glass, barium glass or strontium glass is preferably used.

The adhesive composition of this invention can be used as an adhesive or a coherent agent for adhering, onto dentine, a dental restorative material such as ceramics, a composite resin cured substance, porcelain or a metal. Alternatively, it can be used also as a pretreatment agent applied on the surface of a metal material for improving the adhesive property before applying an adhesive or a coherent agent. The adhesive composition of this invention can be used together with a dental composite resin, a filling material such as a compomer, a dental bonding material, an adhesive material such as resin cement, glass ionomer cement, resin-modified glass ionomer cement, zinc phosphate cement, polycarboxylate cement or silicate cement, a heat-curing resin and an autopolymer resin, and also can be used together with a commercially available tooth plane cleaning agent such as an acid etchant or hypochlorite.

EMBODIMENTS

The present invention will now be described in detail on the basis of preferred embodiments thereof, and it is noted that the invention is not limited to the following embodiments. Abbreviations used in description below stand for the following:

[Phosphate Group-Containing Monomer (a) Including a Fluorocarbon Group]

Chemical Formula 2:

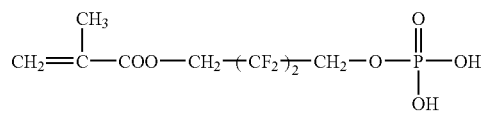

MF4P

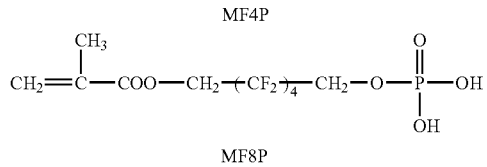

MF8P

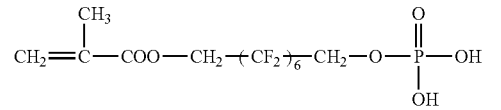

MF12P

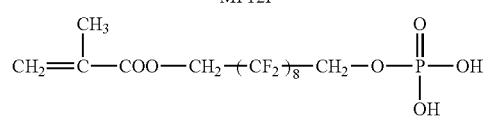

MF16P

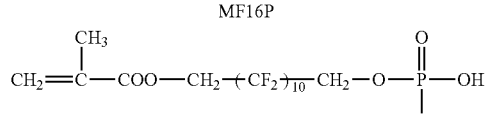

MF20P

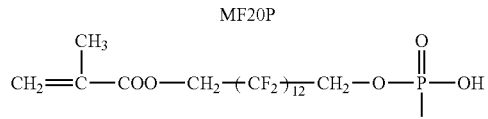

MF24P

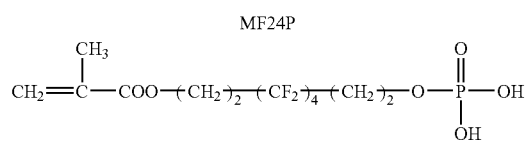

MF8H8P

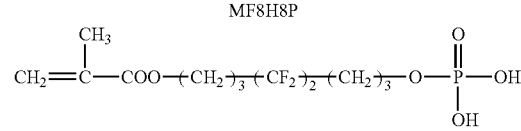

MF4H12P

[Phosphate Group-Containing Monomer not Including a Fluorocarbon Group]
MBP: 4-methacryloyloxybutyl dihydrogenphosphate
MHP: 6-methacryloyloxyhexyl dihydrogenphosphate
MOP: 8-methacryloyloxyoctyl dihydrogenphosphate
[Solvent]
UDMA: [2,2,4-trimethylhexamethylenebis(2-carbamoyloxyethyl)]dimethacrylate
Bis-GMA: bisphenol A diglycidyl methacrylate
3G: triethylene glycol dimethacrylate
GDM: 1,3-dimethacryloyloxy-2-hydroxypropane
PDM: 1,2-bis(3-methacryloyloxy-2-hydroxypropoxy)ethane
MMA: methyl methacrylate
[Silane Coupling Agent]
3 MPS: 3-methacryloyloxypropyltrimethoxysilane
[Polymerization Initiator and Polymerization Promoter]
TMDPO: 2,4,6-trimethylbenzoyldiphenylphosphine oxide
CQ: camphorquinone
BPO: benzoyl peroxide
TPSS: sodium 2,4,6-triisopropylbenzenesulfinate
DEPT: N,N-bis(2-hydroxyethyl)-p-toluidine
DMABE: ethyl 4-N,N-dimethylaminobenzoate
[Polymerization Inhibitor (Stabilizing Agent)]
BHT: 2,6-di-t-butyl-4-methylphenol Preparation Example 1

Methacrylic acid (140 g=1.6 mol), 2,2,3,3-tetrafluoro-1,4-butanediol (259 g=1.6 mol), p-toluenesulfonic acid (15 g) and 2,2'-methylenebis(4-ethyl-6-t-butylphenol) (0.6 g) were placed in a one-liter three-necked flask and heated under reduced pressure of 100 through 150 mmHg to 90° C., and the reaction is continuously caused while blowing oxygen into the mixture for several hours until evaporation of water ceased. When the evaporation of water ceased, the thus obtained reaction solution was cooled to room temperature, moved to a separating funnel and washed with a 5% sodium carbonate aqueous solution until the wash water became alkaline. Subsequently, the reaction solution thus obtained after the alkali washing was further washed with water (300 ml) five times. After anhydrous sodium sulfate was added to the resultant reaction solution for dehydration, hydroquinone monomethyl ether (hereinafter referred to as "MEHQ") (30 mg) was added thereto, and the resultant solution was heated to 80° C. for taking away remaining moisture through distillation, so as to obtain a mixture (245 g) of methacrylic monoester and methacrylic diester. This mixture was analyzed by high performance liquid chromatography (hereinafter referred to as the "HPLC"), and it was found that the monoester content was 75 mol % and that the residual amount of diol was 0.5 wt % or less.

Preparation Example 2

A solution in which phosphorus oxychloride (55 g=0.36 mol) was dissolved in ethyl ether (100 ml) was placed in a 1-liter reactor and was cooled to −40° C. The methacrylic ester mixture synthesized in Preparation example 1 (100 g; with a methacrylic monoester content of 0.3 mol) and triethylamine (37 g=0.36 mol) were dissolved in ethyl ether (100 ml), and the resultant was placed in a 300-ml dropping funnel, which was connected to the aforementioned reactor. The ethyl ether solution of phosphorus oxychloride contained in the reactor was vigorously stirred and the solution in the dropping funnel was slowly dropped while blowing a dried nitrogen gas into the solution in the reactor. The reaction solution contained in the reactor was kept at −30° C. for 3 hours after completing the dropping, and thereafter, the temperature was increased to 0° C. Subsequently, while stirring the reaction solution contained in the reactor, water (30 g) was dropped from the dropping funnel, and subsequently, a solution of triethylamine (72.9 g=0.72 mol) dissolved in ethyl ether (100 ml) was dropped. The reaction solution contained in the reactor was kept at 0° C. and continuously stirred for 10 hours after completing the dropping. Thereafter, MEHQ (10 mg) was added to a filtrate obtained by filtering separated hydrochloride of triethylamine with a glass filter, and the resultant was heated to 40° C. for distillation to take away ethyl ether under reduced pressure, so as to obtain a nonvolatile liquid residue. This nonvolatile liquid residue was dispersed in water (200 ml) and the resultant solution was neutralized by adding sodium carbonate (65 g=0.6 mol) in limited amounts while vigorously stirring and cooling with ice, and after foaming was stopped, the resultant solution was moved to a separating funnel to be subjected to extraction cleaning with ethyl ether (100 ml) twice and with chloroform (100 ml) four times. Subsequently, 6 normal HCl was added to the aqueous solution obtained after the extraction cleaning while cooling with ice so as to make the solution acidic, and an oily matter separated in the form of a layer was extracted with ethyl ether three times. The three extracts were mixed, anhydrous sodium sulfate was added thereto for drying, MEHQ (10 mg) was added to the resultant and a solvent was taken away through distillation at a temperature of 40° C. or less, so as to give a hyaline liquid (76 g). It was confirmed through nuclear magnetic resonance analysis, infrared spectroscopic analysis and elemental analysis that the hyaline liquid was MF4P of the aforementioned Chemical Formula 2. The purity of this liquid obtained by the HPLC was 96 through 97%.

Preparation Example 3

A mixture of methacrylic monoester and methacrylic diester was obtained in the same manner as in Preparation example 1 except that 2,2,3,3,4,4,5,5-octafluoro-1,6-hexanediol (419 g=1.6 mol) was used instead of 2,2,3,3-tetrafluoro-1,4-butanediol (259 g=1.6 mol). A hyaline liquid (98 g) was obtained in the same manner as in Preparation example 2 except that this mixture (136 g; with a methacrylic monoester content of 0.3 mol) was used instead of the methacrylic ester mixture synthesized in Preparation example 1 (100 g; with a methacrylic monoester content of 0.3 mol). This hyaline liquid was confirmed to be MF8P of the aforementioned Chemical Formula 2 through the nuclear magnetic resonance analysis, the infrared spectroscopic analysis and the elemental analysis. The purity of the liquid obtained by the HPLC was 97 through 98%.

Preparation Example 4

A mixture of methacrylic monoester and methacrylic diester was obtained in the same manner as in Preparation example 1 except that 2,2,3,3,4,4,5,5,6,6,7,7-dodecafluoro-1,8-octanediol (579 g=1.6 mol) was used instead of 2,2,3,3-tetrafluoro-1,4-butanediol (259 g=1.6 mol). A hyaline solid (123 g) was obtained in the same manner as in Preparation example 2 except that this mixture (163 g; with a methacrylic monoester content of 0.3 mol) was used instead of the methacrylic ester mixture synthesized in Preparation example 1 (100 g; with a methacrylic monoester content of 0.3 mol). This hyaline solid was confirmed to be MF12P of the aforementioned Chemical Formula 2 through the nuclear magnetic resonance analysis, the infrared spectroscopic analysis and the elemental analysis. The purity of the solid obtained by the HPLC was 95 through 96%.

Preparation Example 5

A mixture of methacrylic monoester and methacrylic diester was obtained in the same manner as in Preparation example 1 except that 2,2,3,3,4,4,5,5,6,6,7,7,8,8,9,9-hexadecafluoro-1,10-decanediol (739 g=1.6 mol) was used instead of 2,2,3,3-tetrafluoro-1,4-butanediol (259 g=1.6 mol). A hyaline solid (145 g) was obtained in the same manner as in Preparation example 2 except that this mixture (207 g; with a methacrylic monoester content of 0.3 mol) was used instead of the methacrylic ester mixture synthesized in Preparation example 1 (100 g; with a methacrylic monoester content of 0.3 mol). This hyaline solid was confirmed to be MF16P of the aforementioned Chemical Formula 2 through the nuclear magnetic resonance analysis, the infrared spectroscopic analysis and the elemental analysis. The purity of the solid obtained by the HPLC was 95 through 96%.

Preparation Example 6

A mixture of methacrylic monoester and methacrylic diester was obtained in the same manner as in Preparation example 1 except that 2,2,3,3,4,4,5,5,6,6,7,7,8,8,9,9,10,10,11,11-eicosafluoro-1,12-dodecanediol (899 g=1.6 mol) was used instead of 2,2,3,3-tetrafluoro-1,4-butanediol (259 g=1.6 mol). A hyaline solid (166 g) was obtained in the same manner as in Preparation example 2 except that this mixture (252 g; with a methacrylic monoester content of 0.3 mol) was used instead of the methacrylic ester mixture synthesized in Preparation example 1 (100 g; with a methacrylic monoester content of 0.3 mol). This hyaline solid was confirmed to be MF20P of the aforementioned Chemical Formula 2 through the nuclear magnetic resonance analysis, the infrared spectroscopic analysis and the elemental analysis. The purity of the solid obtained by the HPLC was 95 through 96%.

Preparation Example 7

A mixture of methacrylic monoester and methacrylic diester was obtained in the same manner as in Preparation example 1 except that 2,2,3,3,4,4,5,5,6,6,7,7,8,8,9,9,10,10,11,11,12,12,13,13-tetracosafluoro-1,14-tetradecanediol (1059 g 1.6 mol) was used instead of 2,2,3,3-tetrafluoro-1,4-butanediol (259 g=1.6 mol). A hyaline solid (183 g) was obtained in the same manner as in Preparation example 2 except that this mixture (292 g; with a methacrylic monoester content of 0.3 mol) was used instead of the methacrylic ester mixture synthesized in Preparation example 1 (100 g; with a methacrylic monoester content of 0.3 mol). This hyaline solid was confirmed to be MF24P of the aforementioned Chemical Formula 2 through the nuclear magnetic resonance analysis, the infrared spectroscopic analysis and the elemental analysis. The purity of the solid obtained by the HPLC was 95 through 96%.

Preparation Example 8

A mixture of methacrylic monoester and methacrylic diester was obtained in the same manner as in Preparation example 1 except that 3,3,4,4,5,5,6,6-octafluoro-1,8-octanediol (464 g=1.6 mol) was used instead of 2,2,3,3-tetrafluoro-1,4-butanediol (259 g=1.6 mol). A hyaline solid (102 g) was obtained in the same manner as in Preparation example 2 except that this mixture (153 g; with a methacrylic monoester content of 0.3 mol) was used instead of the methacrylic ester mixture synthesized in Preparation example 1 (100 g; with a methacrylic monoester content of 0.3 mol). This hyaline solid was confirmed to be MF8H8P of the aforementioned Chemical Formula 2 through the nuclear magnetic resonance analysis, the infrared spectroscopic analysis and the elemental analysis. The purity of the solid obtained by the HPLC was 95 through 96%.

Preparation Example 9

A mixture of methacrylic monoester and methacrylic diester was obtained in the same manner as in Preparation example 1 except that 4,4,5,5-octafluoro-1,8-octanediol (348 g=1.6 mol) was used instead of 2,2,3,3-tetrafluoro-1,4-butanediol (259 g=1.6 mol). A hyaline solid (88 g) was obtained in the same manner as in Preparation example 2 except that this mixture (123 g; with a methacrylic monoester content of 0.3 mol) was used instead of the methacrylic ester mixture synthesized in Preparation example 1 (100 g; with a methacrylic monoester content of 0.3 mol). This hyaline solid was confirmed to be MF4H12P of the aforementioned Chemical Formula 2 through the nuclear magnetic resonance analysis, the infrared spectroscopic analysis and the elemental analysis. The purity of the solid obtained by the HPLC was 95 through 96%.

Embodiment 1

An adhesive composition was prepared by dissolving MF4P (1 part by weight) in ethanol (100 parts by weight).

With respect to this adhesive composition, homogeneity was checked in a manner described below and an adhesive test was performed as described below, so as to obtain bond strength and adhesive durability on each of dental restorative materials specified below. The results are listed in Table 1. Each numerical value of tensile bond strength used in Table 1 was obtained as an average value of eight measured values. The tensile bond strength obtained in each of embodiments and comparative examples described below was obtained also by the adhesive test described below, and each numerical value of the tensile bond strength was also obtained as an average value of eight measured values.

<Dental Restorative Materials>
  alumina-based ceramics (manufactured by Nobelbiocare, trade name "Procera (Alumina)")
  zirconia-based ceramics (manufactured by Nobelbiocare, trade name "Procera (Zirconia)")
  gold alloy (manufactured by GC, trade name "Casting Gold M.C. TypeIV")
  gold/silver/palladium alloy (manufactured by GC, trade name "Castwell M.C.")
  nickel/chromium alloy (manufactured by Towa Giken Co., Ltd., trade name NOWCROM)
  silver alloy (manufactured by GC, trade name "miro silver")
  titanium (manufactured by Shofu Inc., trade name "titan 100")
  porcelain (manufactured by VITA, trade name "VITA CELAY BLANKS")
  composite resin cured substance (manufactured by Kuraray Medical Inc., trade name "Clearfil AP-X(A3)")
  hybrid ceramics (manufactured by Kuraray Medical Inc., trade name "Estenia C&B(E1)")

<Homogeneity>

The homogeneity of the prepared adhesive composition was visually observed. The homogeneity of one having transparent appearance was evaluated as ○ (good homogeneity) and the homogeneity of one having opaque appearance was evaluated as x (poor homogeneity). The bond strength depends upon the homogeneity, and a composition with good homogeneity is minimally varied in the bond strength.

<Adhesive Test>

After polishing to smooth an adhesive surface (adherend surface) of an adherend with #1000 silicon carbide paper (manufactured by Nihon Kenshi Co., Ltd.), the surface is dried with a dental air syringe. In order to restrict an adhesion area, a tape with a thickness of 150 in having a hole with a diameter of 5 mm is adhered on the adherend surface. The adhesive composition is applied within the hole and air dried (blown) by using a dental air syringe until the composition loses flowability. A two-paste type photo/chemical polymerization composite resin (manufactured by Kuraray Medical Inc., trade name "Clapearl DC,US") is placed thereon, the resultant is covered with a polyester film, and a slide glass is placed thereon and pressed. Subsequently, the slide glass used for pressing is removed, and the photo/chemical polymerization composite resin is cured by irradiating through the polyester film with a dental light irradiator (manufactured by Morita, trade name "JETLITE 3000") for 20 seconds. One end of a stainless steel cylindrical bar (with a diameter of 7 mm and a length of 2.5 cm) sandblasted with aluminum oxide having an average particle diameter of 50 μm is adhered on the thus obtained cured surface with a commercially available dental resin cement (Manufactured by Kuraray Medical Inc., trade name "Panavia F2.0"), thereby obtaining a test piece, and 30 minutes after the adhesion, the test piece is immersed in distilled water. The number of test pieces thus prepared is 16 in total, and all the test pieces are immersed in distilled water contained in a thermostat kept at 37° C. for 24 hours. In eight of the 16 test pieces, the adhesive strength is measured immediately after the 24-hour immersion for examining the bond strength attained at an early stage of the adhesion. Each of the remaining 8 test pieces is subjected to 20000 thermal cycles in each cycle of which it is immersed alternately in cool water of 4° C. for 1 minute and warm water of 60° C. for 1 minute and is then measured for the tensile bond strength for examining the adhesive durability. The tensile bond strength is measured with an autograph (manufactured by Shimadzu Corporation, trade code "MODELAG-1") with a cross head speed set to 2 mm/min.

Embodiment 2

An adhesive composition was prepared by dissolving MF12P (1 part by weight) in MMA (100 parts by weight), and with respect to the prepared adhesive composition, the aforementioned homogeneity was checked and the tensile bond strengths on the above-described restorative materials were obtained. The results are listed in Table 1.

Embodiment 3

An adhesive composition was prepared by dissolving MF4P (5 parts by weight) in 3G (100 parts by weight), and with respect to the prepared adhesive composition, the aforementioned homogeneity was checked and the tensile bond strengths on the above-described restorative materials were obtained. The results are listed in Table 1.

Embodiment 4

An adhesive composition was prepared by dissolving MF12P (5 parts by weight) in a mixed solvent of ethanol (90 parts by weight) and UDMA (10 parts by weight), and with respect to the prepared adhesive composition, the aforementioned homogeneity was checked and the tensile bond strengths on the above-described restorative materials were obtained. The results are listed in Table 1.

Comparative Example 1

The above-described adhesive test was performed without using an adhesive composition. The results are listed in Table 1.

Comparative Example 2

An adhesive composition was prepared by dissolving MBP (1 part by weight) in ethanol (100 parts by weight), and with respect to the prepared adhesive composition, the aforementioned homogeneity was checked and the tensile bond strengths on the above-described restorative materials were obtained. The results are listed in Table 1. Although an organic group including a polymeric double bond (a methacryloyloxy group) and a phosphate group (a phosphono group) are linked to each other through a bivalent bonding group with a carbon number of 4 in the MBP in the same manner as in the MF4P, the MBP and the MF4P are different from each other because the bonding group of the MF4P is a 2,2,3,3-tetrafluorooxytetramethylene group while the bonding group of the MBP is an oxytetramethylene group.

Comparative Example 3

An adhesive composition was prepared by dissolving MOP (5 parts by weight) in a mixed solvent of ethanol (90 parts by weight) and UDMA (10 parts by weight), and with respect to the prepared adhesive composition, the aforementioned homogeneity was checked and the tensile bond strengths on the above-described restorative materials were obtained. The results are listed in Table 1. Although an organic group including a polymeric double bond (a methacryloyloxy group) and a phosphate group (a phosphono group) are linked to each other through a bivalent bonding group with a carbon number of 8 in the MOP in the same manner as in the MF12P, the MOP and the MF12P are different from each other because the bonding group of the MF12P is a 2,2,3,3,4,4,5,5,6,6,7,7-dodecafluorooxyoctamethylene group while the bonding group of the MOP is an oxyoctamethylene group.

TABLE 1

| | | Emb. 1 | Emb. 2 | Emb. 3 | Emb. 4 | Com. Ex. 1 | Com. Ex. 2 | Com. Ex. 3 |
|---|---|---|---|---|---|---|---|---|
| Adhesive Composition | Acidic group-containing monomer (a) including fluorocarbon group: | | | | | | | |
| | MF4P (parts by weight) | 1 | — | 5 | — | — | — | — |
| | MF12P (parts by weight) | — | 1 | — | 5 | — | — | — |
| | Acidic group-containing monomer not including fluorocarbon group: | | | | | | | |
| | MBP (parts by weight) | — | — | — | — | — | 1 | — |
| | MOP (parts by weight) | — | — | — | — | — | — | 5 |
| | Solvent (b): | | | | | | | |
| | Ethanol (parts by weight) | 100 | — | — | 90 | — | 100 | 90 |
| | MMA (parts by weight) | — | 100 | — | — | — | — | — |
| | 3G (parts by weight) | — | — | 100 | — | — | — | — |
| | UDMA (parts by weight) | — | — | — | 10 | — | — | 10 |
| Adhesive strength (MPa) | | | | | | | | |
| Alumina-based ceramics | 37° C., 1 day after | 26.5 | 26.9 | 25.5 | 26.9 | 2.9 | 23.5 | 23.9 |
| | After thermal cycles | 25.8 | 26.4 | 25.1 | 26.0 | 0 | 6.1 | 6.8 |
| Zirconia-based ceramics | 37° C., 1 day after | 26.7 | 26.9 | 26.9 | 26.1 | 3.1 | 22.5 | 23.1 |
| | After thermal cycles | 26.2 | 26.5 | 26.9 | 26.9 | 0 | 7.2 | 9.9 |

TABLE 1-continued

|  |  | Emb. 1 | Emb. 2 | Emb. 3 | Emb. 4 | Com. Ex. 1 | Com. Ex. 2 | Com. Ex. 3 |
|---|---|---|---|---|---|---|---|---|
| Porcelain | 37° C., 1 day after | 27.5 | 27.9 | 27.5 | 27.5 | 4.8 | 24.7 | 25.1 |
|  | After thermal cycles | 27.1 | 27.6 | 27.2 | 27.4 | 0 | 7.0 | 9.5 |
| Gold alloy | 37° C., 1 day after | 22.5 | 22.8 | 22.5 | 22.9 | 2.1 | 20.5 | 21.5 |
|  | After thermal cycles | 22.1 | 22.4 | 22.2 | 22.8 | 0 | 5.5 | 6.2 |
| Gold/silver/ | 37° C., 1 day after | 22.4 | 22.7 | 22.1 | 22.9 | 2.7 | 21.4 | 21.7 |
| palladium alloy | After thermal cycles | 22.0 | 22.1 | 22.2 | 22.3 | 0 | 6.1 | 6.9 |
| Nickel/chromium | 37° C., 1 day after | 27.3 | 27.5 | 27.5 | 27.4 | 4.9 | 23.5 | 24.5 |
| alloy | After thermal cycles | 27.1 | 27.0 | 26.9 | 27.0 | 0 | 12.8 | 13.1 |
| Titanium alloy | 37° C., 1 day after | 27.2 | 27.5 | 27.3 | 27.5 | 4.2 | 23.7 | 24.1 |
|  | After thermal cycles | 27.0 | 27.1 | 26.9 | 27.2 | 0 | 13.1 | 13.3 |
| Composite resin | 37° C., 1 day after | 27.2 | 27.5 | 27.3 | 27.5 | 5.3 | 23.5 | 23.7 |
| cured substance | After thermal cycles | 27.2 | 27.5 | 27.3 | 27.5 | 0 | 9.1 | 9.5 |
| Hybrid ceramics | 37° C., 1 day after | 24.4 | 24.2 | 24.0 | 24.4 | 5.1 | 22.5 | 23.0 |
|  | After thermal cycles | 23.9 | 24.1 | 24.5 | 24.9 | 0 | 8.3 | 8.9 |
| Homogeneity |  | ◯ | ◯ | ◯ | ◯ | ◯ | ◯ | ◯ |

As shown in Table 1, in the case where an adhesive composition including a phosphate group-containing monomer having a fluorocarbon group (fluoroalkyleneoxy group) (MF4P or MF12P) was used, very high adhesive durability was exhibited on all the dental restorative materials (Embodiments 1 through 4). On the contrary, in the case where an adhesive composition was not used, a photo/chemical polymerization composite resin was peeled off from the surface of an adherend in all the test pieces after the thermal cycle test (Comparative Example 1). Furthermore, in the case where an adhesive composition including the MBP, which has, as the bonding group, an alkyleneoxy group having the same carbon number as the bonding group of the MF4P but not fluorinated, or an adhesive composition including the MOP, which has, as the bonding group, an alkyleneoxy group having the same carbon number as the bonding group of the MF12P but not fluorinated, was used, although a photo/chemical polymerization composite resin remained to be adhered onto an adherend surface after the thermal cycle test, the adhesive strength was largely lowered on all the dental restorative materials after the thermal cycle test, and in particular, the adhesive strength on a dental restorative material except for a base alloy (such as nickel/chromium alloy or titanium alloy) was lowered to be less than 10 MPa (Comparative Examples 2 and 3).

Embodiments 5 Through 9

Five kinds of adhesive compositions were prepared, and with respect to each of the prepared adhesive compositions, the aforementioned homogeneity was checked and the tensile bond strengths on the aforementioned restorative materials were obtained. The compositions of the respective adhesive compositions and the results are listed in Table 2.

Comparative Examples 4 Through 7

Four kinds of adhesive compositions were prepared, and with respect to each of the prepared adhesive compositions, the aforementioned homogeneity was checked and the tensile bond strengths on the aforementioned restorative materials were obtained. The compositions of the respective adhesive compositions and the results are listed in Table 2.

TABLE 2

|  |  | Emb. 5 | Emb. 6 | Emb. 7 | Emb. 8 | Emb. 9 | Com. Ex. 4 | Com. Ex. 5 | Com. Ex. 6 | Com. Ex. 7 |
|---|---|---|---|---|---|---|---|---|---|---|
| Adhesive Composition | Acidic group-containing monomer (a) including fluorocarbon group: |  |  |  |  |  |  |  |  |  |
|  | MF12P (parts by weight) | 1 | 1 | 1 | 1 | — | — | — | — | — |
|  | MF8H8P (parts by weight) | — | — | — | — | 1 | — | — | — | — |
|  | MF4H12P (parts by weight) | — | — | — | — | — | 1 | — | — | — |
|  | Acidic group-containing monomer not including fluorocarbon group: |  |  |  |  |  |  |  |  |  |
|  | MOP (parts by weight) | — | — | — | — | — | — | 1 | 1 | 1 |
|  | Coupling agent (c) |  |  |  |  |  |  |  |  |  |
|  | 3-MPS | 5 | 5 | — | 5 | 5 | 5 | 5 | — | 5 |
|  | Polymerization initiator (d) |  |  |  |  |  |  |  |  |  |
|  | CQ (parts by weight) | — | — | 0.2 | 0.2 | — | — | — | 0.2 | 0.2 |
|  | Polymerization promoter (e) |  |  |  |  |  |  |  |  |  |
|  | DMABE (parts by weight) | — | — | 0.2 | 0.2 | — | — | — | 0.2 | 0.2 |
|  | Solvent (b): |  |  |  |  |  |  |  |  |  |
|  | Ethanol (parts by weight) | 100 | — | 100 | 90 | 100 | 100 | 100 | 100 | 90 |
|  | MMA (parts by weight) | — | 100 | — | 10 | — | — | — | — | 10 |

TABLE 2-continued

| | | Emb. 5 | Emb. 6 | Emb. 7 | Emb. 8 | Emb. 9 | Com. Ex. 4 | Com. Ex. 5 | Com. Ex. 6 | Com. Ex. 7 |
|---|---|---|---|---|---|---|---|---|---|---|
| Adhesive strength (MPa) | | | | | | | | | | |
| Alumina-based ceramics | 37° C., 1 day after | 28.5 | 28.6 | 27.1 | 30.9 | 28.0 | 26.0 | 25.3 | 24.6 | 25.8 |
| | After thermal cycles | 28.8 | 28.4 | 26.6 | 30.0 | 27.9 | 11.9 | 7.8 | 6.2 | 8.3 |
| Zirconia-based ceramics | 37° C., 1 day after | 28.7 | 28.5 | 27.0 | 30.1 | 28.6 | 27.2 | 25.1 | 23.6 | 25.2 |
| | After thermal cycles | 28.9 | 28.2 | 26.7 | 30.9 | 27.5 | 12.1 | 8.0 | 7.3 | 8.1 |
| Porcelain | 37° C., 1 day after | 29.5 | 29.9 | 28.1 | 31.5 | 28.4 | 28.0 | 27.1 | 25.8 | 27.4 |
| | After thermal cycles | 29.4 | 29.6 | 27.9 | 31.4 | 28.5 | 12.3 | 8.8 | 7.2 | 9.1 |
| Gold alloy | 37° C., 1 day after | 23.5 | 23.2 | 22.8 | 23.9 | 21.5 | 20.9 | 21.1 | 20.1 | 21.3 |
| | After thermal cycles | 23.4 | 23.4 | 22.5 | 23.8 | 19.5 | 11.0 | 7.1 | 5.8 | 7.7 |
| Gold/silver/palladium alloy | 37° C., 1 day after | 27.4 | 27.4 | 22.8 | 27.9 | 26.5 | 25.3 | 21.5 | 21.0 | 21.7 |
| | After thermal cycles | 26.3 | 26.1 | 22.2 | 28.3 | 25.0 | 11.6 | 7.1 | 6.3 | 7.4 |
| Nickel/chromium alloy | 37° C., 1 day after | 29.7 | 29.5 | 27.6 | 30.9 | 28.3 | 27.7 | 25.1 | 22.1 | 23.6 |
| | After thermal cycles | 29.5 | 29.5 | 27.3 | 30.5 | 27.5 | 12.0 | 8.0 | 14.3 | 14.5 |
| Titanium alloy | 37° C., 1 day after | 29.6 | 29.2 | 27.8 | 30.6 | 28.0 | 27.6 | 25.2 | 23.2 | 25.2 |
| | After thermal cycles | 29.9 | 29.1 | 27.2 | 30.9 | 27.6 | 11.5 | 9.5 | 13.9 | 14.0 |
| Composite resin cured substance | 37° C., 1 day after | 26.0 | 26.3 | 25.1 | 28.0 | 24.8 | 24.9 | 24.7 | 22.4 | 24.8 |
| | After thermal cycles | 26.3 | 26.5 | 24.3 | 28.1 | 25.5 | 12.1 | 9.1 | 9.2 | 8.9 |
| Hybrid ceramics | 37° C., 1 day after | 31.4 | 31.2 | 24.5 | 31.4 | 29.9 | 28.2 | 28.0 | 26.3 | 28.1 |
| | After thermal cycles | 31.9 | 31.1 | 24.3 | 31.9 | 28.3 | 12.3 | 7.8 | 8.5 | 8.3 |
| Homogeneity | | ○ | ○ | ○ | ○ | ○ | ○ | ○ | ○ | ○ |

As shown in Table 2, in the case where an adhesive composition including a phosphate group-containing monomer having a fluorocarbon group (a fluoroalkyleneoxy group) (MF12P) was used, very high adhesive durability was attained on all the dental restorative materials (Embodiments 5 through 8). Also, in using an adhesive composition including a phosphate group-containing monomer which is represented by Chemical Formula 1 in which p=q=2 and n=4 and a half of the carbon chain is occupied by fluorocarbon groups (MF8H8P), very high adhesive durability was attained (Embodiment 9) as well as in using the adhesive composition including the MF12P (Embodiments 5 through 8). On the contrary, in the case where an adhesive composition including a phosphate group-containing monomer in which p=q=3 and n=2 in Chemical Formula 1 (MF4H12P) was used, the adhesive strength attained after the thermal cycle test was low (Comparative Example 4). Furthermore, in the case where an adhesive composition including MOP, which has, as a bonding group, an alkyleneoxy group with the same carbon number as the bonding group of the MF12P but not fluorinated, was used, although a photo/chemical polymerization composite resin was adhered on an adherend surface after the thermal cycle test, the adhesive strength was largely lowered on all the dental restorative materials after the thermal cycle test, and in particular, the adhesive strength on a dental restorative material except for a base alloy (such as nickel/chromium alloy or titanium alloy) was lowered to be less than 10 MPa (Comparative Examples 5 through 7).

Embodiments 10 Through 13 and Comparative Example 8

Five kinds of adhesive compositions were prepared, and with respect to each of the prepared adhesive compositions, the homogeneity was checked and the tensile bond strengths on the aforementioned restorative materials were obtained. The compositions of the respective adhesive compositions and the results are listed in Table 3. Each value of ρ (standard deviation) shown in Table 3 is a value calculated based on measured results of 8 samples. Since the value of the standard deviation depends upon the homogeneity of a composition, values of the standard deviation are exemplarily shown with respect to part of adherends of Embodiment 12 and Comparative Example 8.

TABLE 3

|  |  | Emb. 10 | Emb. 11 | Emb. 12 | Emb. 13 | Com. Ex. 8 |
|---|---|---|---|---|---|---|
| Adhesive Composition | Acidic group-containing monomer (a) including fluorocarbon group: |  |  |  |  |  |
|  | MF8P (parts by weight) | 1 | — | — | 1 | — |
|  | MF16P (parts by weight) | — | 1 | — | — | — |
|  | MF20P (parts by weight) | — | — | 1 | — | — |
|  | MF24P (parts by weight) | — | — | — | — | 1 |
|  | Coupling agent (c): |  |  |  |  |  |
|  | 3-MPS (parts by weight) | — | — | — | 5 | — |
|  | Polymerization initiator (d): |  |  |  |  |  |
|  | CQ (parts by weight) | — | — | — | 0.2 | — |
|  | Polymerization promoter (e): |  |  |  |  |  |
|  | DMABE (parts by weight) | — | — | — | 0.2 | — |
|  | Solvent (b): |  |  |  |  |  |
|  | Ethanol (parts by weight) | 100 | 100 | 100 | 100 | 100 |
|  | Adhesive strength (MPa) |  |  |  |  |  |
| Alumina-based ceramics | 37° C., 1 day after | 26.8 | 26.9 | 26.8 (σ2.5) | 28.1 | 24.0 (σ7.9) |
|  | After thermal cycles | 26.1 | 26.2 | 26.4 (σ2.1) | 28.8 | 23.5 (σ6.5) |
| Zirconia-based ceramics | 37° C., 1 day after | 26.7 | 26.8 | 26.3 | 28.5 | — |
|  | After thermal cycles | 26.6 | 26.6 | 26.4 | 28.4 | — |
| Porcelain | 37° C., 1 day after | 27.7 | 27.9 | 27.5 (σ2.1) | 29.3 | 26.0 (σ6.4) |
|  | After thermal cycles | 27.3 | 27.4 | 27.5 (σ1.9) | 29.1 | 25.5 (σ7.0) |
| Gold alloy | 37° C., 1 day after | 22.8 | 22.9 | 22.5 | 23.3 | — |
|  | After thermal cycles | 22.4 | 22.5 | 22.7 | 23.1 | — |
| Gold/silver/palladium alloy | 37° C., 1 day after | 22.7 | 23.1 | 23.3 | 27.2 | — |
|  | After thermal cycles | 22.3 | 22.5 | 22.7 | 26.5 | — |
| Nickel/chromium alloy | 37° C., 1 day after | 27.1 | 27.5 | 27.3 | 29.3 | — |
|  | After thermal cycles | 25.3 | 25.5 | 25.9 | 28.1 | — |
| Titanium alloy | 37° C., 1 day after | 27.8 | 27.9 | 28.2 | 29.4 | — |
|  | After thermal cycles | 25.4 | 25.5 | 25.8 | 29.1 | — |
| Composite resin cured substance | 37° C., 1 day after | 24.5 | 24.7 | 24.5 (σ1.5) | 26.1 | 23.5 (σ5.5) |
|  | After thermal cycles | 24.1 | 24.3 | 24.2 (σ2.6) | 25.7 | 24.0 (σ4.9) |
| Hybrid ceramics | 37° C., 1 day after | 24.6 | 24.7 | 24.2 | 30.1 | — |
|  | After thermal cycles | 24.1 | 24.5 | 24.3 | 29.3 | — |
| Homogeneity |  | ○ | ○ | ○ | ○ | X |

As shown in Table 3, in the case where an adhesive composition including a phosphate group-containing monomer having a fluorocarbon group (a fluoroalkyleneoxy group) (MF8P, MF16P or MF20P) was used, very high adhesive durability was attained on all the dental restorative materials (Embodiments 10 through 13). On the other hand, in the case where an adhesive composition including MF24P having a long chain was used, the composition was not completely dissolved in the solvent but heterogeneous, and hence, the bond strength was largely varied.

Comparative Examples 9 Through 11

Three kinds of adhesive compositions were prepared, and with respect to each of the prepared adhesive compositions, the homogeneity was checked and the tensile bond strengths on the aforementioned restorative materials were obtained. The compositions of the respective adhesive compositions and the results are listed in Table 4.

TABLE 4

|  |  | Com. Ex. 9 | Com. Ex. 10 | Com. Ex. 11 |
|---|---|---|---|---|
| Adhesive Composition | Acidic group-containing monomer (a) not including fluorocarbon group: |  |  |  |
|  | MHP (parts by weight) | 1 | 1 | 1 |
|  | Coupling agent (c): |  |  |  |
|  | 3-MPS (parts by weight) | — | 5 | 5 |
|  | Polymerization initiator (d): |  |  |  |
|  | CQ (parts by weight) | — | — | 0.2 |
|  | Polymerization promoter (e): |  |  |  |
|  | DMABE (parts by weight) | — | — | 0.2 |
|  | Solvent (b): |  |  |  |
|  | Ethanol (parts by weight) | 100 | 100 | 100 |
|  | Adhesive strength (MPa) |  |  |  |
| Alumina-based ceramics | 37° C., 1 day after | 24.6 | 26.1 | 26.3 |
|  | After thermal cycles | 6.3 | 7.3 | 7.4 |
| Zirconia-based ceramics | 37° C., 1 day after | 23.6 | 25.3 | 25.5 |
|  | After thermal cycles | 7.6 | 8.2 | 8.6 |
| Porcelain | 37° C., 1 day after | 25.7 | 27.6 | 27.4 |
|  | After thermal cycles | 7.1 | 9.1 | 9.2 |
| Gold alloy | 37° C., 1 day after | 21.8 | 23.3 | 23.1 |
|  | After thermal cycles | 5.7 | 7.6 | 7.9 |
| Gold/silver/palladium alloy | 37° C., 1 day after | 22.6 | 22.9 | 23.1 |
|  | After thermal cycles | 6.5 | 7.5 | 7.9 |
| Nickel/chromium alloy | 37° C., 1 day after | 23.3 | 23.7 | 24.1 |
|  | After thermal cycles | 13.2 | 13.5 | 14.0 |

TABLE 4-continued

|  |  | Com. Ex. 9 | Com. Ex. 10 | Com. Ex. 11 |
|---|---|---|---|---|
| Titanium alloy | 37° C., 1 day after | 23.8 | 25.7 | 25.6 |
|  | After thermal cycles | 13.1 | 13.5 | 14.2 |
| Composite resin | 37° C., 1 day after | 23.2 | 24.9 | 24.8 |
| cured substance | After thermal cycles | 9.3 | 9.5 | 9.2 |
| Hybrid ceramics | 37° C., 1 day after | 22.4 | 23.5 | 24.0 |
|  | After thermal cycles | 6.5 | 7.9 | 8.0 |
| Homogeneity |  | ○ | ○ | ○ |

As shown in Table 4, in the case where an adhesive composition including a phosphate group-containing monomer not including a fluorocarbon group (a fluoroalkyleneoxy group) (MHP) was used, although the photo/chemical polymerization composite resin was adhered on an adherend surface after the thermal cycle test, the adhesive strength was largely lowered on all the dental restorative materials after the thermal cycle test, and in particular, the adhesive strength on a dental restorative material except for a base alloy (such as nickel/chromium alloy or titanium alloy) was lowered to be less than 10 MPa.

Embodiments 14 and 15 and Comparative Examples 12 and 13

Four kinds of two-paste type adhesive compositions were prepared, and with respect to each of the prepared adhesive compositions, the homogeneity was checked, and the tensile bond strengths on the aforementioned restorative materials and the coloring resistance were obtained respectively by an adhesive test and a coloring resistance test described below. It is noted that a paste A and a paste B of each adhesive composition were prepared by simply mixing respective components at room temperature. The components of the respective adhesive compositions are listed in Table 5 and the results are listed in Table 6.

<Adhesive Test>

After polishing to smooth adherend surfaces of two adherends of the same kind with #1000 silicon carbide paper (manufactured by Nihon Kenshi Co., Ltd.), a tape with a thickness of 150 μm having a hole with a diameter of 5 mm is adhered on the adherend surface of one adherend in order to restrict an adhesion area. Subsequently, an adhesive composition is prepared by mixing a paste A and a paste B in equivalent weights, it is applied within the hole, and the adherends of the same kind are adhered to each other so as to fabricate a test piece, and 30 minutes after the adhesion, the test piece is immersed in distilled water. The number of test pieces thus prepared is 16 in total, and all the test pieces are immersed in distilled water contained in a thermostat kept at 37° C. for 24 hours. In eight of the 16 test pieces, the adhesive strength is measured immediately after the 24-hour immersion for examining the bond strength attained at an early stage of the adhesion. Each of the remaining 8 test pieces is subjected to 20000 thermal cycles in each cycle of which it is immersed alternately in cool water of 4° C. for 1 minute and warm water of 60° C. for 1 minute and is then measured for the tensile bond strength for examining the adhesive durability. The tensile bond strength is measured with an autograph (manufactured by Shimadzu Corporation, trade code "MODELAG-1") with a cross head speed set to 2 mm/min.

<Coloring Resistance Test>

A tape (manufactured by 3M, trade name "Scotch Brand Tape") is adhered onto a glass plate, and a frame made of Teflon (registered trademark) having a hole with a diameter of 1 cm and a thickness of 1 mm is placed thereon. An adhesive composition is prepared by mixing a paste A and a paste B in equivalent weights, the adhesive composition is applied within the hole and covered with a polyester film, and a glass plate is placed thereon and slightly pressed. Subsequently, the glass plate used for pressing is removed, and the adhesive composition is cured by irradiating through the polyester film with a dental light irradiator (manufactured by Morita Corporation, trade name "α-light") for 3 minutes. Thereafter, the cured adhesive composition is taken out of the frame of Teflon (registered trademark) to be used as a test piece. A yellow turmeric suspension is prepared by adding turmeric (manufactured by Gaban Com., Ltd.) (0.005 g) in distilled water (100 ml), and the test piece is immersed in this suspension. After immersing the test piece in the suspension contained in a thermostat kept at 37° C. for 18 hours, the test piece is taken out and washed with running water for 1 minute, and the coloring degree of the test piece is visually observed.

TABLE 5

|  |  |  | Emb. 14 | Emb. 15 | Com. Ex. 12 | Com. Ex. 13 |
|---|---|---|---|---|---|---|
| Adhesive Composition | Paste A | Bis-GMA (parts by weight) | 30 | 30 | 30 | 30 |
|  |  | UDMA (parts by weight) | 20 | 20 | 20 | 20 |
|  |  | 3G (parts by weight) | 30 | 25 | 30 | 25 |
|  |  | MF4P (parts by weight) | 20 | — | — | — |
|  |  | MF12P (parts by weight) | — | 25 | — | — |
|  |  | MBP (parts by weight) | — | — | 20 | — |
|  |  | MOP (parts by weight) | — | — | — | 25 |
|  |  | BPO (parts by weight) | 3 | 3 | 3 | 3 |
|  |  | CQ (parts by weight) | 1 | 1 | 1 | 1 |
|  |  | BHT (parts by weight) | 0.05 | 0.05 | 0.05 | 0.05 |
|  |  | Silane-treated quartz powder (parts by weight) | 300 | 300 | 300 | 300 |
|  | Paste B | Bis-BMA (parts by weight) | 30 | 30 | 30 | 30 |
|  |  | UDMA (parts by weight) | 30 | 30 | 30 | 30 |
|  |  | GDM (parts by weight) | 10 | 10 | 10 | 10 |
|  |  | PDM (parts by weight) | 10 | 10 | 10 | 10 |
|  |  | 3G (parts by weight) | 20 | 20 | 20 | 20 |
|  |  | TPSS (parts by weight) | 0.5 | 0.5 | 0.5 | 0.5 |
|  |  | DEPT (parts by weight) | 1 | 1 | 1 | 1 |
|  |  | DMABE (parts by weight) | 1 | 1 | 1 | 1 |
|  |  | BHT (parts by weight) | 0.05 | 0.05 | 0.05 | 0.05 |
|  |  | Barium glass powder (parts by weight) | 300 | 300 | 300 | 300 |

TABLE 6

|  |  | Emb. 14 | Emb. 15 | Com. Ex. 12 | Com. Ex. 13 |
|---|---|---|---|---|---|
| Alumina-based ceramics | 37° C., 1 day after | 27.1 | 28.4 | 22.5 | 23.1 |
|  | After thermal cycles | 26.2 | 28.2 | 6.8 | 8.3 |
| Zirconia-based ceramics | 37° C., 1 day after | 27.3 | 28.7 | 23.1 | 24.2 |
|  | After thermal cycles | 26.5 | 28.6 | 7.0 | 8.4 |
| Porcelain | 37° C., 1 day after | 27.2 | 29.9 | 24.0 | 26.6 |
|  | After thermal cycles | 27.5 | 29.3 | 6.5 | 7.1 |
| Gold alloy | 37° C., 1 day after | 22.1 | 23.5 | 20.3 | 21.7 |
|  | After thermal cycles | 22.0 | 23.2 | 5.9 | 6.5 |
| Gold/silver/ palladium alloy | 37° C., 1 day after | 22.3 | 27.9 | 22.7 | 21.5 |
|  | After thermal cycles | 21.8 | 26.8 | 4.9 | 6.6 |
| Nickel/chromium alloy | 37° C., 1 day after | 25.8 | 26.2 | 25.1 | 25.3 |
|  | After thermal cycles | 25.4 | 25.6 | 13.1 | 14.0 |
| Titanium alloy | 37° C., 1 day after | 25.8 | 25.9 | 24.2 | 25.4 |
|  | After thermal cycles | 25.6 | 25.7 | 12.4 | 13.1 |
| Composite resin cured substance | 37° C., 1 day after | 23.9 | 25.0 | 22.5 | 23.1 |
|  | After thermal cycles | 23.4 | 25.3 | 8.8 | 7.7 |
| Hybrid ceramics | 37° C., 1 day after | 24.8 | 25.4 | 22.1 | 24.1 |
|  | After thermal cycles | 24.5 | 25.6 | 8.8 | 7.1 |
| Homogeneity |  | ○ | ○ | ○ | ○ |
| Coloring resistance |  | Citron | Citron | Yellow | Yellow |

As shown in Table 6, in the case where an adhesive composition including a phosphate group-containing monomer having a fluorocarbon group (a fluoroalkyleneoxy group) (MF4P or MF12P) was used, very high adhesive durability was attained on all the dental restorative materials (Embodiments 14 and 15). On the contrary, in the case where an adhesive composition including MBP, which has, as a bonding group, an alkyleneoxy group with the same carbon number as the bonding group of the MF4P but not fluorinated, was used (Comparative Example 12) or in the case where an adhesive composition including MOP, which has, as a bonding group, an alkyleneoxy group with the same carbon number as the bonding group of the MF12P but not fluorinated, was used (Comparative Example 13), although the photo/chemical polymerization composite resin was adhered on the adherend surface after the thermal cycle test, the adhesive strength was largely lowered on all the dental restorative materials, and in particular, the adhesive strength on a dental restorative material except for a base alloy (such as nickel/chromium alloy or titanium alloy) was lowered to be less than 10 MPa.

Furthermore, as shown in Table 6, in the case where the adhesive composition including a phosphate group-containing monomer having a fluorocarbon group (a fluoroalkyleneoxy group) (MF4P or MF12P) was used (Embodiment 14 or 15), although the composition was colored with yellow derived from camphorquinone, the coloring degree was not largely different between before and after the immersion in the turmeric suspension. On the contrary, in the case where the adhesive composition including the MBP was used (Comparative Example 12) or the adhesive composition including the MOP was used (Comparative Example 13), the degree of coloring (yellowing) with turmeric was large.

Embodiments 16 and 17 and Comparative Example 14 and 15

Four kinds of adhesive compositions were prepared, and with respect to each of the prepared adhesive compositions, the homogeneity was checked and the tensile bond strength on dentine (enamel and ivory) was obtained by an adhesive test described below. The compositions of the respective adhesive compositions and the results are shown in Table 7.

<Adhesive Test>

An anterior tooth of a bovine is wet polished for smoothing with #1000 silicon carbide paper (manufactured by Nihon Kenshi Co., Ltd.) so as to expose an enamel surface or an ivory surface, and moisture remaining on the surface is then blown off by using a dental air syringe. An adhesive tape with a thickness of approximately 150 μm having a hole with a diameter of 3 mm is adhered on the exposed enamel or ivory surface, an adhesive composition is applied within the hole with a brush, and after allowing the adhesive composition to stand for 20 seconds, it is dried with an air syringe until the applied adhesive composition loses flowability. Subsequently, the resultant adhesive composition is irradiated with light for 10 seconds by using a dental light irradiator (manufacture by Morita, trade name "JETLITE 3000"). Thereafter, a commercially available photopolymerization composite resin (manufactured by Kuraray Medical Inc., trade name "Clearfil AP-X") is placed thereon, the resultant is covered with a polyester film, and a slide glass is placed thereon and pressed. Under this condition, the resultant is irradiated with light by using the above-described light irradiator for 20 seconds so as to cure the photopolymerization composite resin. One end of a stainless steel cylindrical bar (with a diameter of 5 mm and a length of 1.5 cm) sandblasted with aluminum oxide having an average particle diameter of 50 μm is adhered on the thus obtained cured surface with a commercially available dental resin cement (Manufactured by Kuraray Medical Inc., trade name "Panavia F2.0"), thereby obtaining a test piece, and 30 minutes after the adhesion, the test piece is immersed in distilled water. The number of test pieces thus prepared is 16 in total, and all the test pieces are immersed in distilled water contained in a thermostat kept at 37° C. for 24 hours. In eight of the 16 test pieces, the adhesive strength is measured immediately after the 24-hour immersion for examining the bond strength attained at an early stage of the adhesion. Each of the remaining 8 test pieces is subjected to 20000 thermal cycles in each cycle of which it is immersed alternately in cool water of 4° C. for 1 minute and warm water of 60° C. for 1 minute and is then measured for the tensile bond strength for examining the adhesive durability. The tensile bond strength is measured with an autograph (the above-described "MODELAG-1") with a cross head speed set to 2 mm/min.

TABLE 7

| | | Emb. 16 | Emb. 17 | Com. Ex. 14 | Com. Ex. 15 |
|---|---|---|---|---|---|
| Adhesive Composition | Acidic group-containing monomer (a) including fluorocarbon group: | | | | |
| | M4P (parts by weight) | 15 | — | — | — |
| | M12P (parts by weight) | — | 15 | — | — |
| | Acidic group-containing monomer not including fluorocarbon group: | | | | |
| | MBP (parts by weight) | — | — | 15 | — |
| | MOP (parts by weight) | — | — | — | 15 |
| | Polymerization initiator (d): | | | | |
| | TMDPO (parts by weight) | 2 | 2 | 2 | 2 |
| | CQ (parts by weight) | 1 | 1 | 1 | 1 |
| | Polymerization promoter (e): | | | | |
| | DMABE (parts by weight) | 1 | 1 | 1 | 1 |
| | Additional component: | | | | |
| | BHT (parts by weight) | 0.05 | 0.05 | 0.05 | 0.05 |
| | Solvent (b): | | | | |
| | HEMA (parts by weight) | 45 | 45 | 45 | 45 |
| | Distilled water (parts by weight) | 10 | 10 | 10 | 10 |
| | Bis-GMA (parts by weight) | 30 | 30 | 30 | 30 |
| Adhesive strength (MPa) | | | | | |
| Enamel | 37° C., 1 day after | 17.5 | 18.0 | 15.6 | 16.3 |
| | After thermal cycles | 16.9 | 17.8 | 9.6 | 9.8 |
| Ivory | 37° C., 1 day after | 15.4 | 16.1 | 14.4 | 15.1 |
| | After thermal cycles | 14.9 | 15.2 | 8.8 | 8.9 |
| Homogeneity | | ○ | ○ | ○ | ○ |

As shown in Table 7, in the case where an adhesive composition including a phosphate group-containing monomer having a fluorocarbon group (a fluoroalkyleneoxy group) (MF4P or MF12P) was used (Embodiment 16 or 17), very high adhesive durability was attained on dentine On the contrary, in the case where an adhesive composition including a phosphate group-containing monomer having an alkyleneoxy group not fluorinated (MBP or MOP) was used (Comparative Example 14 or 15), although the photopolymerization composite resin was adhered on the dentine after the thermal cycle test, the adhesive strength on the dentine was lowered to be less than 10 MPa after the thermal cycle test.

The invention claimed is:

1. An adhesive composition comprising:
at least one phosphate group-containing monomer (a) having a fluorocarbon group represented by Chemical Formula 1; and
at least one solvent (b),

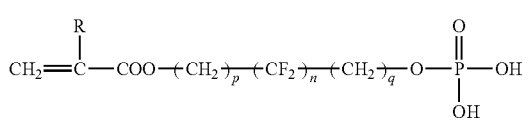

(1)

wherein R is a hydrogen atom or a methyl group, n, p and q are natural numbers, $2 \leq n \leq 10$, $p+q \leq n$ and $p+q+n \leq 13$.

2. The adhesive composition according to claim 1, further comprising at least one coupling agent (c).

3. The adhesive composition according to claim 1, further comprising at least one polymerization initiator (d), at least one polymerization promoter (e), or a combination thereof.

4. The adhesive composition according to claim 1, further comprising at least one filler (f).

5. The adhesive composition according to claim 1, wherein said at least one phosphate group-containing monomer (a) is present in an amount of from 0.001 to 99 wt % based on the total weight of the composition.

6. The adhesive composition according to claim 1, wherein said at least one phosphate group-containing monomer (a) is present in an amount of from 0.01 to 90 wt % based on the total weight of the composition.

7. The adhesive composition according to claim 1, wherein said at least one phosphate group-containing monomer (a) is present in an amount of from 0.1 to 85 wt % based on the total weight of the composition.

8. The adhesive composition according to claim 1, wherein said solvent (b) is a solvent having a boiling point of 150° C. or less at normal pressure.

9. The adhesive composition according to claim 1, wherein said solvent (b) is a solvent having a boiling point of 110° C. or less at normal pressure.

10. The adhesive composition according to claim 1, wherein said solvent (b) comprises at least one selected from the group consisting of water; ethanol; methanol; 1-propanol; isopropyl alcohol; acetone; methyl ethyl ketone; ethyl acetate; methyl acetate; ethyl propionate; methyl methacrylate; 1,2-dimethoxyethane; 1,2-di ethoxyethane; tetrahydrofuran; heptane; hexane; toluene; chloroform; and dichloromethane.

11. The adhesive composition according to claim 2, wherein said coupling agent (c) comprises at least one selected from the group consisting of methyltrimethoxysilane; methyltriethoxysilane; methyltrichlorosilane; dimethyldichlorosilane; trimethylchlorosilane; vinyltrimethoxysilane; vinyltriethoxysilane; vinyltrichlorosilane; vinyltriacetoxysilane; vinyltri(β-methoxyethoxy)silane; 3-(meth)acryloyloxypropyltrimethoxysilane; 3-(meth)acryloyloxypropyltriethoxysilane; 6-(meth)acryloyloxyhexyltrimethoxysilane; 6-(meth)acryloyloxyhexyltriethoxysilane; 10-(meth)acryloyloxydecyltrimethoxysilane; 10-(meth)acryloyloxydecyltriethoxysilane; 11-(meth)acryloyloxyundecyltrimethoxysilane; 11-(meth)acryloyloxyundecyltriethoxysilane; 3-(meth)acryloyloxypropylpentamethyldisiloxane; 3-chloropropyltrimethoxysilane; mercaptopropyltrimethoxysilane; hexamethyldisilazane; isopropyl triisostearoyl titanate; isopropyl trioctanoyl titanate; isopropyl isostearoyl diacryl titanate; isopropyl tridecyl benzene sulfonyl titanate; isopropyl dimethacryloyl isostearoyl titanate; isopropyl tricumyl phenyl titanate; and acetoalkoxy aluminum diisopropylate.

12. The adhesive composition according to claim 3, wherein said at least one polymerization initiator (d) is present in an amount of from 0.01 to 10 wt %, based on the total weight of the composition.

13. The adhesive composition according to claim 3, wherein said at least one polymerization initiator (d) is present in an amount of from 0.1 to 5 wt %, based on the total weight of the composition.

14. The adhesive composition according to claim 3, wherein said at least one polymerization initiator (d) comprises at least one member selected from the group consisting of an α-diketone, a ketal, a thioxanthone, an acylphosphine oxide, a coumarin, a halomethyl-s-triazine, and an organic peroxide.

15. The adhesive composition according to claim 3, wherein said at least one polymerization promoter (e) comprises at least one member selected from the group consisting of a tertiary amine, an aldehyde, a compound having a thiol group, sulfinic acid, and a salt of a sulfinic acid.

16. The adhesive composition according to claim 3, wherein said at least one polymerization promoter (e) is present in an amount of from 0.01 to 10 wt %, based on the total weight of the composition.

17. The adhesive composition according to claim 3, wherein said at least one polymerization promoter (e) is present in an amount of from 0.05 to 7 wt %, based on the total weight of the composition.

18. The adhesive composition according to claim 3, wherein said at least one polymerization promoter (e) is present in an amount of from 0.1 to 5 wt %, based on the total weight of the composition.

* * * * *